United States Patent
Yang et al.

(10) Patent No.: US 10,748,268 B2
(45) Date of Patent: Aug. 18, 2020

(54) RETINAL VESSEL IMAGE ENHANCEMENT METHOD AND SYSTEM

(71) Applicant: SHENZHEN UNIVERSITY, Shenzhen, Guangdong (CN)

(72) Inventors: Xuan Yang, Guangdong (CN); Junhao Wu, Guangdong (CN); Jihong Pei, Guangdong (CN)

(73) Assignee: SHENZHEN UNIVERSITY, Shenzhen (CN)

(*) Notice: Subject to any disclaimer, the term of this patent is extended or adjusted under 35 U.S.C. 154(b) by 102 days.

(21) Appl. No.: 16/221,781

(22) Filed: Dec. 17, 2018

(65) Prior Publication Data
US 2019/0122350 A1   Apr. 25, 2019

Related U.S. Application Data

(63) Continuation of application No. PCT/CN2016/099026, filed on Sep. 14, 2016.

(51) Int. Cl.
| | |
|---|---|
| G06T 5/50 | (2006.01) |
| G06T 7/00 | (2017.01) |
| G06T 5/00 | (2006.01) |
| G06T 7/136 | (2017.01) |
| A61B 3/00 | (2006.01) |
| G06K 9/64 | (2006.01) |

(Continued)

(52) U.S. Cl.
CPC .............. *G06T 5/50* (2013.01); *A61B 3/0025* (2013.01); *G06K 9/64* (2013.01); *G06T 5/002* (2013.01); *G06T 7/0012* (2013.01); *A61B 3/12* (2013.01); *G06T 5/009* (2013.01); *G06T 7/11* (2017.01); *G06T 7/136* (2017.01); *G06T 2207/20024* (2013.01); *G06T 2207/20192* (2013.01); *G06T 2207/30041* (2013.01); *G06T 2207/30101* (2013.01)

(58) Field of Classification Search
None
See application file for complete search history.

(56) References Cited

U.S. PATENT DOCUMENTS 10,402,965 B1 * 9/2019 Bagherinia ........... G06T 7/0012
10,636,145 B2 * 4/2020 Bagherinia ............... G06T 7/32
(Continued)

*Primary Examiner* — Nancy Bitar

(57) ABSTRACT

An retinal vessel image enhancement method comprises: constructing a blood vascular dictionary; applying Frangi-based filtering to retinal vessel images, deciding blood vessels in a second image sub-block belong to wide or thin vessels by directional filtering, and setting residual error weight and residual error threshold of a vascular region; calculating inner products between the second image sub-block and each first image sub-block, selecting a first image sub-block with maximum inner product, and calculating its corresponding sparse coefficient; calculating residual error image, and calculating the residual error of the vascular region according to the residual error weight of the vascular region, when the residual error is greater than the residual error threshold, the residual error image is set as a second image sub-block, repeating and calculating residual error; reconstructing the second image sub-block according to the sparse coefficient, then restructuring each reconstructed second image sub-block, obtaining enhanced retinal vessel images.

18 Claims, 3 Drawing Sheets

(51) Int. Cl.
*A61B 3/12* (2006.01)
*G06T 7/11* (2017.01)

(56) References Cited

U.S. PATENT DOCUMENTS

| | | | | |
|---|---|---|---|---|
| 2009/0136112 A1* | 5/2009 | Bismuth | ............... | G06T 5/002 382/132 |
| 2010/0085447 A1* | 4/2010 | Kanemitsu | ............... | G06T 5/20 348/241 |
| 2016/0239956 A1* | 8/2016 | Kang | ............... | G06T 7/12 |

* cited by examiner

RETINAL VESSEL IMAGE ENHANCEMENT METHOD AND SYSTEM

CROSS REFERENCE TO RELATED APPLICATIONS

The present application is a continuation-application of International (PCT) Patent Application No. PCT/CN2016/099026, filed on Sep. 14, 2016, the entire contents of which are hereby incorporated by reference.

TECHNICAL FIELD

The present invention relates to the field of image processing technology, and more particularly to a method and system for retinal vessel image enhancement.

BACKGROUND

Retinal imaging is one of the important means of medical aided diagnosis and treatment, which can directly or indirectly determine a variety of ocular diseases by analyzing eyeball blood vessel images. In ocular images, there exist a variety of retinal vessels with varying degrees of thickness, more clear and accurate retinal vessel images can be obtained by enhancing these images, thereby facilitating aided clinical diagnosis.

There are many methods for retinal vessel image enhancement, in general, the most frequently used methods are as follows:

Neighborhood smoothing method, it calculates an average between grayscale of a certain pixel and that of its neighbors in an image, and uses the average value as the grayscale value of the pixel. The advantage of this method is its simplicity, and its disadvantage is that it can make the retinal vessel image blurred, significantly decreasing the clarity of blood vessels.

Edge-preserving smoothing method, namely design different templates, and calculate variances of the grayscale of neighborhood pixels to a certain pixel point in an image, then select a template with minimum variance and take the average grayscale value of pixels contained in the template as the grayscale value of the pixel. The advantage of this method is that it can preferably preserve edges, and its disadvantage is that the target is a linear structure in the retinal vessel image, it is difficult to distinguish noise from target by analysis of variance.

Multiple images averaging method, it chooses multiple images of eyeball blood vessels taken from the same person, and performs the average processing. The advantage of this method is that it can suppress noise to a certain extent, and its disadvantage is that it requires multiple images of eyeball blood vessels, not applicable to a single retinal vessel image.

Frangi-based filtering image enhancement, it enhances a linear structure using eigenvector directions and eigenvalues of Hessian matrix in the linear structure, however, such methods can lead to loss of gracile and thin vessels.

Image denoising methods based on sparse representation, they can get a redundant dictionary by training, then reconstruct the original image according to sparse coefficients, thereby obtain a noise-suppressed image due to no noise in the selected dictionary atoms. This method possesses better noise suppression effects, however, there still exists a problem of loss of gracile and thin vessels when it is applied to the issue of retinal vessel image enhancement.

Thus it can be seen that the existing methods for retinal vessel image enhancement are not able to better reserve thin vessels at the same time of enhancing retinal vessels.

SUMMARY

In the present invention, the technical problem to be solved is to provide a method and system for retinal vessel image enhancement, designed to overcome the shortage of methods for retinal vessel image enhancement in the prior art that are not able to better reserve thin vessels at the same time of enhancing retinal vessels. The invention is realized as the following:

A method for retinal vessel image enhancement, comprising the following steps:

Step A: constructing a blood vascular dictionary using retinal vessel learning images, the above-mentioned blood vascular dictionary comprises a preset number of first image sub-blocks;

Step B: applying the Frangi-based filtering to the retinal vessel images to be enhanced, and dividing the obtained images having undergone Frangi-based filtering into a plurality of second image sub-blocks overlapped each other;

Step C: applying directional filtering to the second image sub-block by means of a directional filter, and deciding that the retinal vessels contained in the second image sub-block belong to wide vessels or thin vessels based on directional filtering results;

Step D: determining a vascular region in the second image sub-block, and setting residual error weight and residual error threshold of a vascular region in the second image sub-block according to retinal vessel types contained in the second image sub-block;

Step E: calculating the inner products between the second image sub-block and each first image sub-block in the blood vascular dictionary, determining a first image sub-block with maximum inner product among them, and calculating the sparse coefficient corresponding to the first image sub-block with maximum inner product;

Step F: calculating a residual error image according to the first image sub-block with maximum inner product and the second image sub-block, and calculating the residual error of the vascular region in the second image sub-block according to the residual error weight of the vascular region;

Step G: when the norm of the residual error is greater than the residual error threshold, setting the residual error image as the second image sub-block, and jump to Step E, otherwise, jump to Step H;

Step H: reconstructing the second image sub-block according to the sparse coefficient;

Step I: reconstructing the retinal vessel image according to each reconstructed second image sub-block, and thereby obtaining an enhanced retinal vessel image.

Furthermore, the Step A comprises the sub-steps of:

Sub-step A1: partitioning the retinal vessel learning image into several first image sub-blocks with the same size; and the number of first image sub-blocks is greater than the set number;

Sub-step A2: calculating all the inner products of every two first image sub-blocks;

Sub-step A3: selecting the preset number of first image sub-blocks with minimum inner product, and constructing the blood vascular dictionary.

Furthermore, the Step B comprises the sub-steps of:

Sub-step B1: supposing the retinal vessel image to be enhanced as $I(x, y)$, and letting $G(x, y; \sigma)$ be a two-dimensional Gaussian function at scale $\sigma$, smoothing the retinal vessel image I(x, y) to be enhanced using the two-dimensional Gaussian function, thereby obtaining a smoothed image $I_o(x, y)$:

$I_o(x, y) = I(x, y) \otimes G(x, y; \sigma)$, where $$G(x, y; \sigma) = \frac{1}{(\sqrt{2\pi}\,\sigma)^2} e^{-\frac{x^2+y^2}{2\sigma^2}},$$

and $\otimes$ denotes a convolutional operation;

Sub-step B2: calculating a Hessian matrix $H_\sigma(x, y)$ at point (x, y) and scale $\sigma$ in the smoothed image $I_o(x, y)$:

$$H_\sigma(x, y) = \begin{bmatrix} \frac{\partial I_\sigma^2(x,y)}{\partial x^2} & \frac{\partial I_\sigma^2(x,y)}{\partial x \partial y} \\ \frac{\partial I_\sigma^2(x,y)}{\partial x \partial y} & \frac{\partial I_\sigma^2(x,y)}{\partial y^2} \end{bmatrix};$$

Sub-step B3: performing an eigenvalue analysis of the Hessian matrix $H_\sigma(x, y)$, then obtaining the eigenvalues $\lambda_1$ and $\lambda_2$, ordered as $|\lambda_1| < |\lambda_2|$; accordingly, the vascular feature at scale s can be expressed by:

$$v_0(s) = \begin{cases} e^{-\frac{R_\beta^2}{2\beta}} \cdot \left(1 - e^{-\frac{S^2}{2c^2}}\right) & \lambda_2 \leq 0 \\ 0 & \lambda_2 > 0 \end{cases};$$

Where $$R_\beta = \frac{|\lambda_1|}{|\lambda_2|},$$

$S = \sqrt{\lambda_1^2 + \lambda_2^2}$, $\beta$ and C are the preset constants;

Sub-step B4: In a multiscale framework, selecting the maximum value of $v_0(s)$ at each scale as a Frangi-based filtering result v of the retinal vessel image I(x, y) to be enhanced:

$v = \max_{s_{min} \leq s \leq s_{max}} v_0(s)$

Where $s_{min}$ and $s_{max}$ denote the minimum and maximum scales, respectively;

Sub-step B5: dividing the Frangi-based filtering result v into a plurality of second image sub-blocks overlapped each other.

Furthermore, the Step C comprises the sub-steps of:

Sub-step C1: setting up 8 directional filters in the directions $\theta_1 = 0, \theta_2 = \frac{\pi}{8}, \theta_3 = \frac{\pi}{4}, \theta_4 = \frac{3\pi}{8}, \theta_5 = \frac{\pi}{2}, \theta_6 = \frac{5\pi}{8}, \theta_7 = \frac{3\pi}{4}$ and $\theta_8 = \frac{7\pi}{8},$ respectively;

Sub-step C2: assuming that $\Omega_1$ is a vascular region by the directional filter in the direction $\theta_i$, $\Omega_2$ is a non-vascular region, the respective energy $posE_{\theta_i}$ and $negE_{\theta_i}$ of the two region is calculated as follows:

$posE_{\theta_i} = \sum_{x=1}^{N_1} \sum_{y=1}^{N_1} |v(x,y)|^2, (x,y) \in \Omega_1;$ $negE_{\theta_i} = \sum_{x'=1}^{N_2} \sum_{y'=1}^{N_2} |v(x',y')|^2, (x',y') \in \Omega_2;$ where v(x, y) is the value of the Frangi-based filtering result v at point (x, y), $N_1$ is the number of pixels in $\Omega_1$, and $N_2$ is the number of pixels in $\Omega_2$;

Sub-step C3: calculating the energy difference between $posE_{\theta_i}$ and $negE_{\theta_i}$:

$E\theta_i = posE_{\theta_i} - negE_{\theta_i};$

Sub-step C4: determining the maximum energy difference among the above-mentioned 8 directions:

$E_{max} = \max_{i=1,2,\ldots,8} E\theta_i;$

Sub-step C5: deciding blood vessel types based on the $E_{max}$, when $E_{max} \geq T$, the retinal vessel image contained in the second image sub-block belongs to wide vessels, otherwise it belongs to thin vessels.

Furthermore, the Step D comprises the sub-steps of:

Sub-step D1: taking the vascular region by the directional filter corresponding to the maximum energy difference among the 8 directions as a vascular region $\Omega_1$, and taking the non-vascular region by the directional filter corresponding to the maximum energy difference among the 8 directions as a non-vascular region $\Omega_2$;

Sub-step D2: for the second image sub-block containing an retinal vessel image that belongs to wide vessels, setting the residual error weight of the vascular region $\Omega_1$ in the second image sub-block to 1, such that the residual error threshold $T_R = T_1$; for the second image sub-block containing an retinal vessel image that belongs to thin vessels, setting its residual error weight of the vascular region $\Omega_1$ to $1/v_{max}$, such that the residual error threshold $T_R = T_2$, where $v_{max}$ denotes the maximum value among Frangi-based filtering results of the second image sub-block.

Furthermore, the Step E comprises the sub-steps of:

Sub-step E1: vectorizing the second image sub-block as x, and letting $d_i$ be first No. i image sub-block in the blood vascular dictionary;

Sub-step E2: taking a first image sub-block corresponding to the largest one of inner products between each first image sub-block in the blood vascular dictionary and the second image sub-block x as the selected No. 1 first image sub-block $d_{r0}$:

$d_{r0} = \arg\max_{i \in (1,2,\ldots,k)} |\langle x, d_i \rangle|;$

Where k denotes the number of first image sub-blocks in the blood vascular dictionary, $r_0$ denotes an index number of the dictionary, and $\langle x, d_i \rangle$ denotes the computation of inner product between x and $d_i$;

Sub-step E3: calculating the sparse coefficient $\alpha_{r0}$ corresponding to the first image sub-block $d_{r0}$:

$\alpha_{r0} = \langle x, d_{r0} \rangle.$

Furthermore, the Step F comprises the sub-steps of:

Sub-step F1: calculating the residual error image R of the vascular region in the second image sub-block:

$R = x - \langle x, d_{r0} \rangle d_{r0};$

Sub-step F2: multiplying the residual error R by the residual error weight of the vascular region in the second image sub-block, and obtaining the weighted sum as the final residual error of vascular region in the second image sub-block.

Furthermore, the reconstructed second image sub-block is defined as:

$\hat{x} = \sum_{r0 \in S} d_{r0} \alpha_{r0}$

Where S denotes a set of multiple sparse coefficients determined by multiple execution of Step E, $d_{ro}$ denotes a first image sub-block with maximum inner product determined by execution of Step E each time and $\alpha_{ro}$ denotes a sparse coefficient corresponding to $d_{ro}$.

Furthermore, the Step I comprises the following:

Merge non-overlapping parts of all the reconstructed second image sub-blocks, thereby obtaining a complete enhanced retinal vessel image.

A system for retinal vessel image enhancement, comprising:

Blood vascular dictionary constructing module, which is configured to construct a blood vascular dictionary using retinal vessel learning images, the blood vascular dictionary comprises a preset number of first image sub-blocks;

Image filtering and dividing module, which is configured to apply the Frangi-based filtering to a retinal vessel image to be enhanced, and divide the enhanced retinal vessel images into a plurality of second image sub-blocks overlapped each other;

Blood vessel type determining module, which is configured to apply directional filtering to the second image sub-block by means of a directional filter, and decide that the blood vessels contained in the second image sub-block belong to wide vessels or thin vessels based on directional filtering results;

Vascular region and its residual error weight and residual error threshold determining module, which is configured to determine a vascular region in the second image sub-block, and set residual error weight and residual error threshold of a vascular region in the second image sub-block according to blood vessel types contained in the second image sub-block;

Sparse coefficient calculating module, which is configured to calculate the inner products between the second image sub-block and each first image sub-block in the blood vascular dictionary, determine a first image sub-block with maximum inner product among them, and calculate the sparse coefficient corresponding to the first image sub-block with maximum inner product;

Vascular region residual error calculating module, which is configured to calculate a residual error image according to the first image sub-block with maximum inner product and the second image sub-block, and calculate the residual error of the vascular region in the second image sub-block according to the residual error weight of the vascular region;

Jumping module, which is configured to, when the norm of the residual error is greater than the residual error threshold, set the residual error image as the second image sub-block, and jump to the sparse coefficient calculating module, otherwise, jump to second image sub-block reconstructing module;

Second image sub-block reconstructing module, which is configured to reconstruct the second image sub-block according to the sparse coefficient;

Retinal vessel image reconstructing module, which is configured to reconstruct the retinal vessel image according to each reconstructed second image sub-block, and thereby obtaining an enhanced retinal vessel image.

Furthermore, the blood vascular dictionary constructing module comprises:

Retinal vessel learning image dividing module, which is configured to partition the retinal vessel learning image into several first image sub-blocks with the same size; and the number of first image sub-blocks is greater than the set number;

First image sub-block inner product module, which is configured to calculate all the inner products of every two first image sub-blocks;

Blood vascular dictionary constructing submodule, which is configured to select the preset number of first image sub-blocks with minimum inner product, and construct the blood vascular dictionary.

Furthermore, the image filtering and dividing module comprises:

Smooth filtering module, which is configured to define the retinal vessel image to be enhanced as I(x, y), and let G(x, y; σ) be a two-dimensional Gaussian function at scale σ, smooth the retinal vessel image I(x, y) to be enhanced using the two-dimensional Gaussian function, thereby obtaining a smoothed image $I_\sigma(x, y)$:

$I_\sigma(x, y) = I(x, y) \otimes G(x, y; \sigma)$, where $$G(x, y; \sigma) = \frac{1}{\left(\sqrt{2\pi}\,\sigma\right)^2} e^{-\frac{x^2+y^2}{2\sigma^2}},$$

and $\otimes$ denotes a convolutional operation;

Hessian matrix calculating module, which is configured to calculate a Hessian matrix $H_\sigma(x, y)$ at point (x, y) and scale σ in the smoothed image $I_\sigma(x, y)$:

$$H_\sigma(x, y) = \begin{bmatrix} \frac{\partial I_\sigma^2(x, y)}{\partial x^2} & \frac{\partial I_\sigma^2(x, y)}{\partial x \partial y} \\ \frac{\partial I_\sigma^2(x, y)}{\partial x \partial y} & \frac{\partial I_\sigma^2(x, y)}{\partial y^2} \end{bmatrix};$$

Eigenvalue analyzing module, which is configured to perform an eigenvalue analysis of the Hessian matrix $H_\sigma(x, y)$, then obtain the eigenvalues $\lambda_1$ and $\lambda_2$, ordered as $|\lambda_1| < |\lambda_2|$; accordingly, the vascular feature at scale s can be expressed by:

$$v_0(s) = \begin{cases} e^{-\frac{R_\beta^2}{2\beta}} \cdot \left(1 - e^{-\frac{S^2}{2c^2}}\right) & \lambda_2 \leq 0 \\ 0 & \lambda_2 > 0 \end{cases};$$

Where $$R_\beta = \frac{|\lambda_1|}{|\lambda_2|},$$

$S = \sqrt{\lambda_1^2 + \lambda_2^2}$, β and C are the preset constants;

Frangi-based filtering result generating module, which is configured to select the maximum value of $v_0(s)$ at each scale as a Frangi-based filtering result v of the retinal vessel image I(x, y) to be enhanced:

$v = \max_{s_{min} \leq s \leq s_{max}} v_0(s)$

Where $s_{min}$ and $s_{max}$ denote the minimum and maximum scales, respectively;

Second image sub-block dividing module, which is configured to divide the Frangi-based filtering result v into a plurality of second image sub-blocks overlapped each other.

Furthermore, the blood vessel type determining module comprises:

Directional filter setting module, which is configured to set up 8 directional filters in the directions $\theta_1=0$, $$\theta_2 = \frac{\pi}{8}, \theta_3 = \frac{\pi}{4}, \theta_4 = \frac{3\pi}{8}, \theta_5 = \frac{\pi}{2}, \theta_6 = \frac{5\pi}{8}, \theta_7 = \frac{3\pi}{4} \text{ and } \theta_8 = \frac{7\pi}{8},$$

respectively;

Energy calculating module, which is configured to, assuming that $\Omega_1$ is a vascular region by the directional filter in the direction $\theta_i$, $\Omega_2$ is a non-vascular region, thus calculate the respective energy $posE_{\theta_i}$ and $negE_{\theta_i}$ of the two region as follows:

$$posE_{\theta_i} = \Sigma_{x=1}^{N1}\Sigma_{y=1}^{N1}|v(x,y)|^2, (x,y) \in \Omega_1;$$

$$negE_{\theta_i} = \Sigma_{x'=1}^{N2}\Sigma_{y'=1}^{N2}|v(x',y')|^2, (x',y') \in \Omega_2;$$

where $v(x, y)$ is the value of the Frangi-based filtering result v at point $(x, y)$, $N_1$ is the number of pixels in $\Omega_1$, and $N_2$ is the number of pixels in $\Omega_2$;

Energy difference calculating module, which is configured to calculate the energy difference between $posE_{\theta_i}$ and $negE_{\theta_i}$:

$$E\theta_i = posE_{\theta_i} - negE_{\theta_i};$$

Maximum energy difference determining module, which is configured to determine the maximum energy difference among the above-mentioned 8 directions:

$$E_{max} = \max_{i=1,2,\ldots,8} E\theta_i;$$

Blood vessel type determining submodule, which is configured to decide blood vessel types based on the $E_{max}$, if $E_{max} \geq T$, the retinal vessel image contained in the second image sub-block belongs to wide vessels, otherwise it belongs to thin vessels.

Furthermore, the vascular region and its residual error weight and residual error threshold determining module comprises:

Vascular region determining module, which is configured to take the vascular region by the directional filter corresponding to the maximum energy difference among the 8 directions as a vascular region $\Omega_1$, and take the non-vascular region by the directional filter corresponding to the maximum energy difference among the 8 directions as a non-vascular region $\Omega_2$;

Residual error weight and residual error threshold determining module is configured to, for the second image sub-block containing an retinal vessel image that belongs to wide vessels, set the residual error weight of the vascular region $\Omega_1$ to 1, such that the residual error threshold $T_R = T_1$; for the second image sub-block containing an retinal vessel image that belongs to thin vessels, set its residual error weight of the vascular region $\Omega_1$ to $1/v_{max}$, such that the residual error threshold $T_R = T_2$, where $v_{max}$ denotes the maximum value among Frangi-based filtering results of the second image sub-block.

Furthermore, the sparse coefficient calculating module comprises:

Image vectorizing module, which is configured to vectorize the second image sub-block as x, and take $d_i$ as first No. i image sub-block in the blood vascular dictionary;

First image sub-block selecting module, which is configured to take a first image sub-block corresponding to the largest one of inner products between each first image sub-block in the blood vascular dictionary and the second image sub-block x as the selected No. 1 first image sub-block $d_{r0}$:

$$d_{r0} = \arg\max_{i \in (1,2,\ldots,k)} |\langle x, d_i \rangle|;$$

Where k denotes the number of first image sub-blocks in the blood vascular dictionary, $r_0$ denotes an index number of the dictionary, and $\langle x, d_i \rangle$ denotes the computation of inner product between x and $d_i$;

Sparse coefficient calculating submodule, which is configured to calculate the sparse coefficient $\alpha_{r0}$ corresponding to the first image sub-block $d_{r0}$:

$$\alpha_{r0} = \langle x, d_{r0} \rangle.$$

Furthermore, the vascular region residual error calculating module comprises:

Residual error preliminarily calculating module, which is configured to calculate the residual error image R of the vascular region in the second image sub-block:

$$R = x - \langle x, d_{r0} \rangle d_{r0};$$

Residual error weighting module, which is configured to multiply the residual error R by the residual error weight of the vascular region in the second image sub-block, and obtain the weighted sum as the final residual error of vascular region in the second image sub-block.

Furthermore, the reconstructed second image sub-block is defined as:

$$\hat{x} = \Sigma_{r0 \in S} d_{r0} \alpha_{r0}$$

Where S denotes a set of multiple sparse coefficients determined by the sparse coefficient calculating module multiple times, $d_{r0}$ denotes a first image sub-block with maximum inner product determined by the sparse coefficient calculating module each time and $\alpha_{r0}$ denotes a sparse coefficient corresponding to $d_{r0}$.

Furthermore, the retinal vessel image reconstructing module is specifically used to:

merge non-overlapping parts of all the reconstructed second image sub-blocks, thereby obtaining a complete enhanced retinal vessel image.

The present invention constructs a blood vascular dictionary using retinal vessel learning images; divides blood vessels in a second image sub-block into wide and thin vessels by means of directional filtering, sets residual error weight and residual error threshold of a vascular region according to wide and thin blood vessels; calculates the inner products between the second image sub-block and each first image sub-block in the dictionary, selects the first image sub-block with maximum inner product, and calculates its corresponding sparse coefficient; calculates the residual error of the vascular region in the second image sub-block according to the residual error weight of the vascular region in the selected first image sub-block, if the residual error is greater than the residual error threshold, repeats a process of selecting the first image sub-block and calculating residual error; reconstructs the second image sub-block according to the sparse coefficient, and restructures each reconstructed second image sub-block, finally obtains enhanced retinal vessel images. The present invention reduces background noise and avoids loss of thin vessels brought about by blood vessel enhancement using Frangi-based filtering in the prior art, achieving the enhancement of retinal vessel images and improving the visual effects of retinal vessel images, which can be used for pretreatment of retinal vessel image analysis.

DESCRIPTION OF THE EMBODIMENTS

In order to make the purpose, technical solutions and advantages of this invention clearer, the present invention will now be further described in detail hereinafter with reference to the drawings and embodiments.

Figure 1:
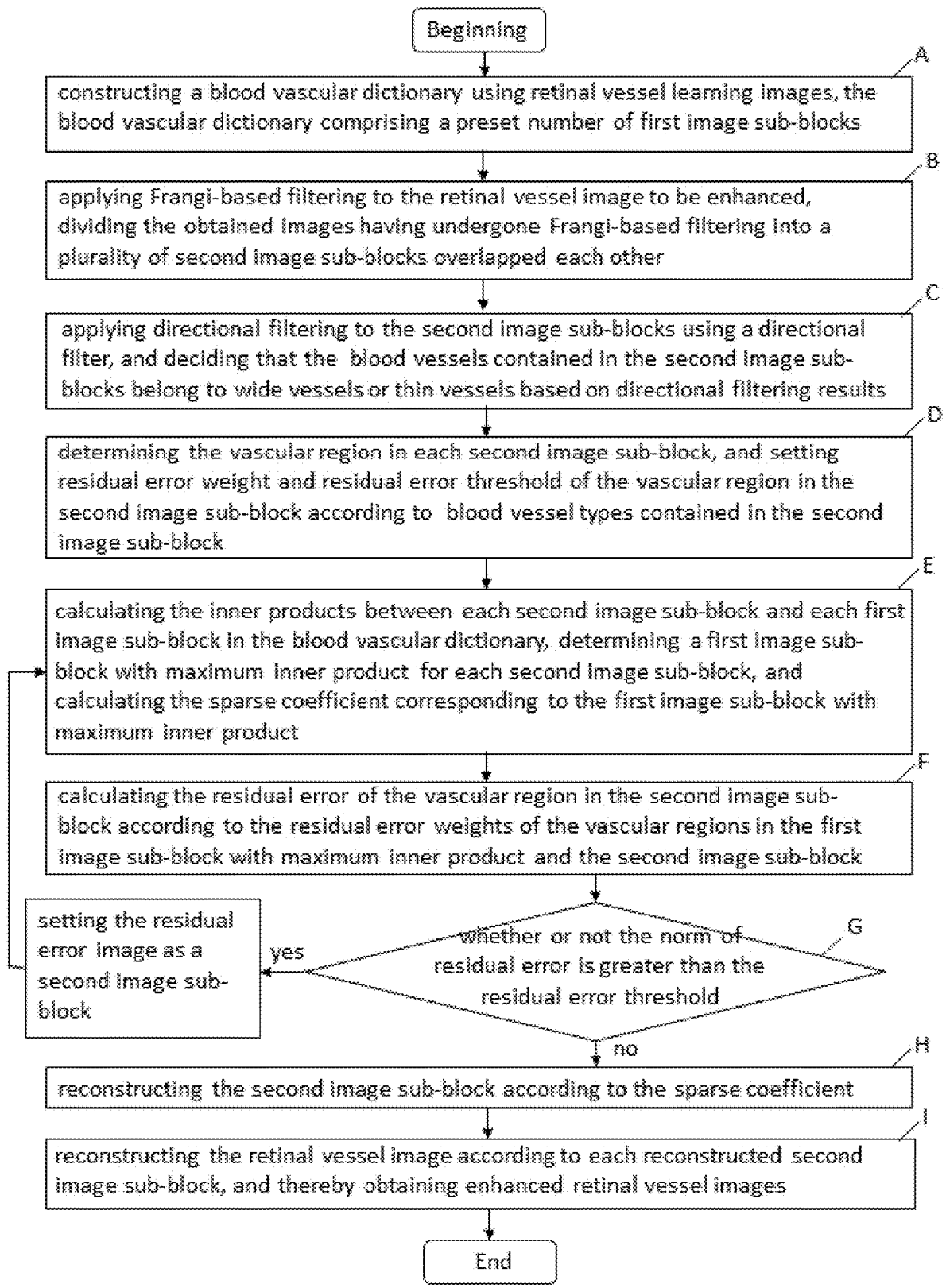
FIG. 1 shows an overall flowchart of the method for retinal vessel image enhancement provided in the present invention.

As shown in FIG. 1, the method for retinal vessel image enhancement provided in the present invention, comprising the following steps:

Step A: constructing a blood vascular dictionary using retinal vessel learning images, the above-mentioned blood vascular dictionary comprises a preset number of first image sub-blocks.

The Step A specifically comprises the sub-steps of:

Sub-step A1: partitioning the retinal vessel learning image into several first image sub-blocks of the same size; and the number of first image sub-blocks should be greater than the preset number. The retinal vessel learning image can be partitioned into a plurality of first image sub-blocks with a size of 8*8 according to artificially partitioned results of the retinal vessel learning image, moreover, these first image sub-blocks should include retinal vessel image features such as wide vessels, gracile and thin vessels, and highlighted parts.

Sub-step A2: calculating all the inner products of every two first image sub-blocks; the smaller the inner product is, the lower degree of similarity between two first image sub-blocks.

Sub-step A3: selecting the preset number of first image sub-blocks with minimum inner product, and constructing the blood vascular dictionary. Let K be a set number, such that select K most dissimilar first image sub-blocks and construct a blood vascular dictionary.

Step B: applying the Frangi-based filtering to the retinal vessel images to be enhanced, and dividing the obtained images having undergone Frangi-based filtering into a plurality of second image sub-blocks overlapped each other.

The Step B specifically comprises the sub-steps of:

Sub-step B1: defining the retinal vessel image to be enhanced as I(x, y), and let G(x, y; σ) be a two-dimensional Gaussian function at scale σ, smoothing the retinal vessel image I(x, y) to be enhanced using the two-dimensional Gaussian function, thereby obtaining a smoothed image $I_\sigma(x, y)$:

$I_\sigma(x, y) = I(x, y) \otimes G(x, y; \sigma)$, where $$G(x, y; \sigma) = \frac{1}{(\sqrt{2\pi}\,\sigma)^2} e^{-\frac{x^2+y^2}{2\sigma^2}},$$

and $\otimes$ denotes a convolutional operation;

Sub-step B2: calculating a Hessian matrix $H_\sigma(x, y)$ at point (x, y) and scale σ in the smoothed image $I_\sigma(x, y)$:

$$H_\sigma(x, y) = \begin{bmatrix} \frac{\partial I_\sigma^2(x, y)}{\partial x^2} & \frac{\partial I_\sigma^2(x, y)}{\partial x \partial y} \\ \frac{\partial I_\sigma^2(x, y)}{\partial x \partial y} & \frac{\partial I_\sigma^2(x, y)}{\partial y^2} \end{bmatrix}.$$

Sub-step B3: performing an eigenvalue analysis of the Hessian matrix $H_\sigma(x, y)$, then obtaining the eigenvalues $\lambda_1$ and $\lambda_2$, ordered as $|\lambda_1|<|\lambda_2|$; if point (x, y) belongs to a tubular structure, such that $|\lambda_1|\approx 0$, and the value of $|\lambda_2|$ tends to be greater, accordingly, the vascular feature at scale s can be expressed by:

$$v_0(s) = \begin{cases} e^{-\frac{R_\beta^2}{2\beta}} \cdot \left(1 - e^{-\frac{S^2}{2c^2}}\right) & \lambda_2 \leq 0 \\ 0 & \lambda_2 > 0 \end{cases};$$

Where $$R_\beta = \frac{|\lambda_1|}{|\lambda_2|},$$

$S=\sqrt{\lambda_1^2+\lambda_2^2}$, β and C are the preset constants;

Sub-step B4: In a multiscale framework, selecting the maximum value of $v_0(s)$ at each scale as a Frangi-based filtering result v of the retinal vessel image I(x, y) to be enhanced:

$$v = \max_{s_{min} \leq s \leq s_{max}} v_0(s)$$

Where $s_{min}$ ands $s_{max}$ denote the minimum and maximum scales, respectively;

Sub-step B5: dividing the Frangi-based filtering result v into a plurality of second image sub-blocks overlapped each other.

Step C: applying directional filtering to the second image sub-block by means of a directional filter, and deciding that the blood vessels contained in the second image sub-block belong to wide vessels or thin vessels based on directional filtering results.

Figure 3:
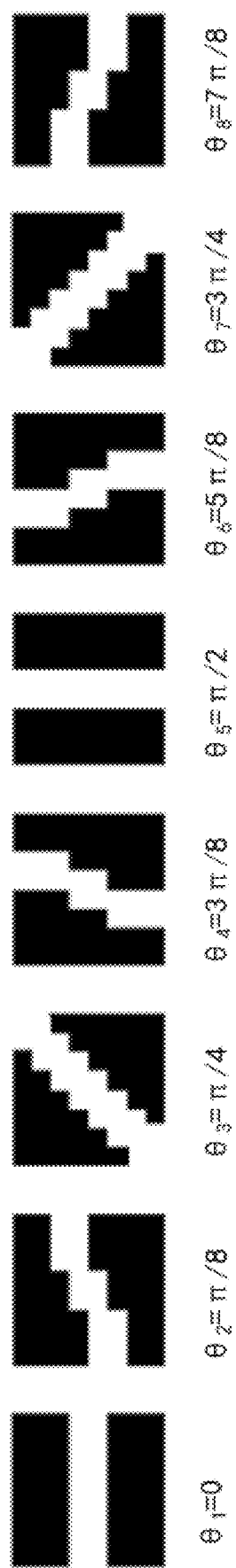
FIG. 3 shows a directional diagram of 8 directional filters.

The Step C specifically comprises the sub-steps of:

Sub-step C1: setting up 8 directional filters in the directions $\theta_1=0$, $$\theta_2 = \frac{\pi}{8}, \theta_3 = \frac{\pi}{4}, \theta_4 = \frac{3\pi}{8}, \theta_5 = \frac{\pi}{2}, \theta_6 = \frac{5\pi}{8}, \theta_7 = \frac{3\pi}{4} \text{ and } \theta_8 = \frac{7\pi}{8},$$

respectively (as shown in FIG. 3).

Sub-step C2: assuming that $\Omega_1$ is a vascular region (white region) by the directional filter in the direction $\theta_i$, $\Omega_2$ is a non-vascular region (black region), the respective energy $posE_{\theta_i}$ and $negE_{\theta_i}$ of the two region is calculated as follows:

$posE_{\theta_i} = \Sigma_{x=1}^{N_1} \Sigma_{y=1}^{N_1} |v(x,y)|^2, (x,y) \in \Omega_1;$ $negE_{\theta_i} = \Sigma_{x'=1}^{N_2} \Sigma_{y'=1}^{N_2} |v(x',y')|^2, (x',y') \in \Omega_2;$ where v(x, y) is the value of the Frangi-based filtering result v at point (x, y), $N_1$ is the number of pixels in $\Omega_1$, and $N_2$ is the number of pixels in $\Omega_2$.

Sub-step C3: calculating the energy difference between $posE_{\theta_i}$ and $negE_{\theta_i}$:

$$E\theta_i = posE_{\theta_i} - negE_{\theta_i};$$

Sub-step C4: determining the maximum energy difference among the above-mentioned 8 directions:

$$E_{max} = \max_{i=1,2,\ldots,8} E\theta_i$$

Sub-step C5: deciding blood vessel types based on the $E_{max}$, if $E_{max} \geq T$, the retinal vessel image contained in the second image sub-block belongs to wide vessels, otherwise it belongs to thin vessels. Where T denotes a preset value.

Step D: determining a vascular region in the second image sub-block, and setting residual error weight and residual error threshold of a vascular region in the second image sub-block according to blood vessel types contained in the second image sub-block.

The Step D specifically comprises the sub-steps of:

Sub-step D1: taking the vascular region by the directional filter corresponding to the maximum energy difference (namely the directional filter corresponding to $E_{max}$ in the direction $\theta_i$) among the 8 directions as a vascular region $\Omega_1$, and taking the non-vascular region by the directional filter corresponding to the maximum energy difference (namely the directional filter corresponding to $E_{max}$ in the direction $\theta_i$) among the 8 directions as a non-vascular region $\Omega_2$.

Sub-step D2: for the second image sub-block containing an retinal vessel image that belongs to wide vessels, setting the residual error weight of the vascular region $\Omega_1$ in the second image sub-block to 1, such that the residual error threshold $T_R = T_1$; for the second image sub-block containing an retinal vessel image that belongs to thin vessels, setting its residual error weight of the vascular region $\Omega_1$ to $1/v_{max}$, such that the residual error threshold $T_R = T_2$, where $v_{max}$ denotes the maximum value among Frangi-based filtering results of the second image sub-block.

The Step D can further comprises the sub-steps of:

Sub-step D3: setting the selected index set S of first image sub-block to an empty set, such that $S = \phi$, then add the index number $r_0$ of the selected first image sub-block $d_{r0}$ into the set S, such that $S = S \cup r0$.

Step E: calculating the inner products between the second image sub-block and each first image sub-block in the blood vascular dictionary, determining a first image sub-block with maximum inner product among them, and calculating the sparse coefficient corresponding to the first image sub-block with maximum inner product.

The Step E specifically comprises the sub-steps of:

Sub-step E1: vectorizing the second image sub-block as x, and let $d_i$ be first No. i image sub-block in the blood vascular dictionary.

Sub-step E2: taking a first image sub-block corresponding to the largest one of inner products between each first image sub-block in the blood vascular dictionary and the second image sub-block x as the selected No. 1 first image sub-block $d_{r0}$:

$$d_{r0} = \arg\max_{i \in (1,2,\ldots,k)} |<x, d_i>|;$$

Where k denotes the number of first image sub-blocks in the blood vascular dictionary, $r_0$ denotes an index number of the dictionary, and $<x,d_i>$ denotes the computation of inner product between x and $d_i$;

Sub-step E3: calculating the sparse coefficient $\alpha_{r0}$ corresponding to the first image sub-block $d_{r0}$:

$$\alpha_{r0} = <x, d_{r0}>.$$

add the index number $r_0$ of the selected first image sub-block $d_{r0}$ into the set S, such that $S = S \cup r0$.

Step F: calculating a residual error image according to the first image sub-block with maximum inner product and the second image sub-block, and calculating the residual error of the vascular region in the second image sub-block according to the residual error weight of the vascular region.

The Step F specifically comprises the sub-steps of:

Sub-step F1: calculating the residual error image R of the vascular region in the second image sub-block:

$$R = x - <x, d_{r0}> d_{r0};$$

Sub-step F2: multiplying the residual error R by the residual error weight of the vascular region in the second image sub-block, and obtaining the weighted sum as the final residual error of vascular region in the second image sub-block.

Step G: when the norm of the residual error is greater than the residual error threshold, setting the residual error image as the second image sub-block, and jumping to Step E, otherwise, jumping to Step H. That is to say, in the Step F, if the norm $\|R\|$ of the residual error R is greater than the residual error threshold $T_R$, jump to Step E, otherwise, jump to Step H.

Step H: reconstructing the second image sub-block according to the sparse coefficient; the reconstructed second image sub-block is defined as:

$$\hat{x} = \sum_{r0 \in S} d_{r0} \alpha_{r0}$$

Where S denotes a set of multiple sparse coefficients determined by multiple execution of Step E, $d_{r0}$ denotes a first image sub-block with maximum inner product determined by execution of Step E each time and $\alpha_{r0}$ denotes a sparse coefficient corresponding to $d_{r0}$.

Step I: reconstructing the retinal vessel image according to each reconstructed second image sub-block, and thereby obtaining an enhanced retinal vessel image.

The Step I comprises the following:

merging non-overlapping parts of all the reconstructed second image sub-blocks, thereby obtaining a complete enhanced retinal vessel image.

Figure 2:
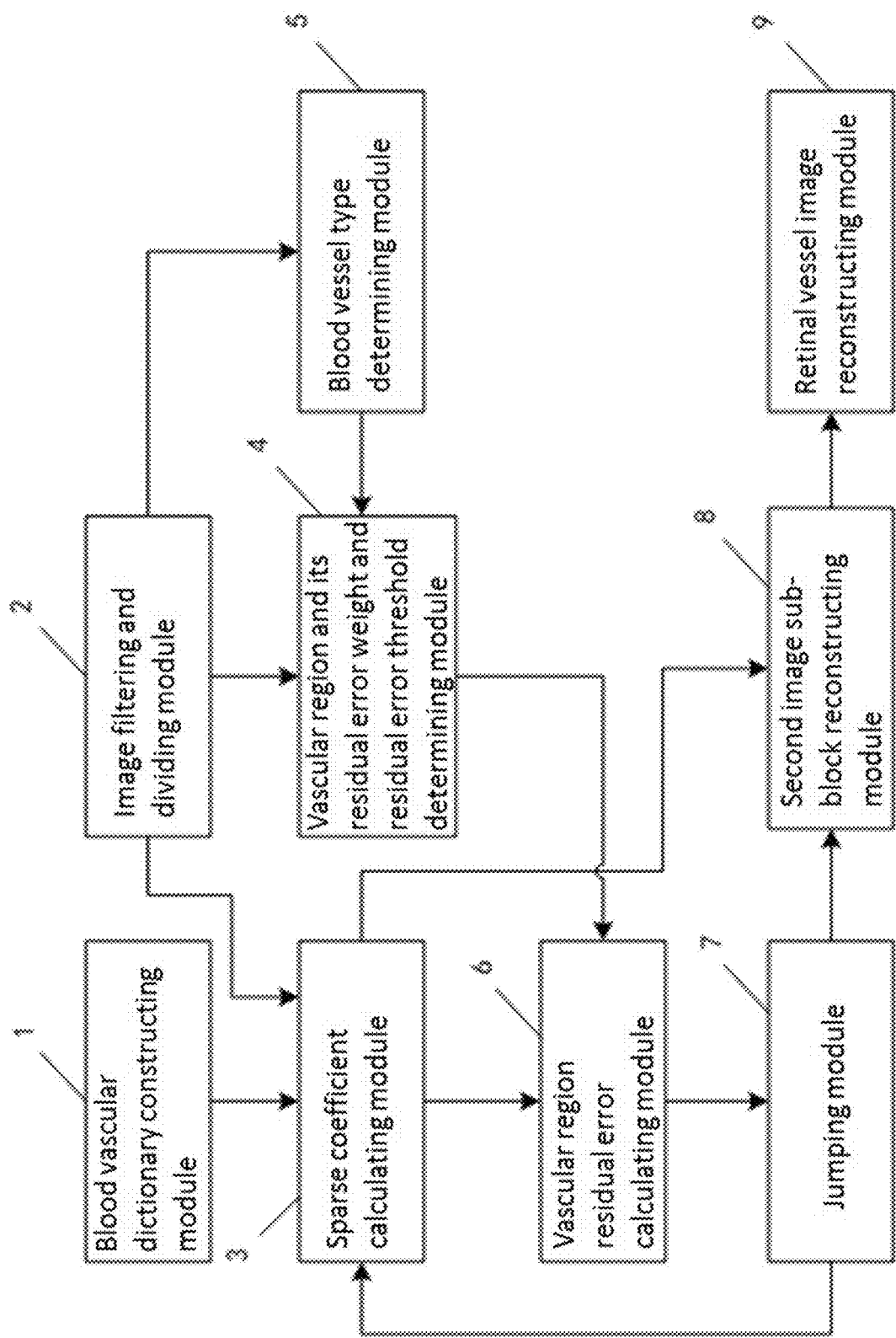
FIG. 2 shows an overall constitute diagram of the system for retinal vessel image enhancement provided in the present invention.

As shown in FIG. 2, based on the aforementioned method for retinal vessel image enhancement, the present invention also provides a system for retinal vessel image enhancement, comprising: blood vascular dictionary constructing module 1, image filtering and dividing module 2, blood vessel type determining module 5, vascular region and its residual error weight and residual error threshold determining module 4, sparse coefficient calculating module 3, vascular region residual error calculating module 6, jumping module 7, second image sub-block reconstructing module 8, and retinal vessel image reconstructing module 9.

Blood vascular dictionary constructing module 1 is configured to construct a blood vascular dictionary using retinal vessel learning images, and the blood vascular dictionary comprises a preset number of first image sub-blocks. Blood vascular dictionary constructing module 1 comprises retinal vessel learning image dividing module, first image sub-block inner product module, and blood vascular dictionary constructing sub-module.

Retinal vessel learning image dividing module is configured to partition the retinal vessel learning image into a plurality of first image sub-blocks with the same size; and the number of first image sub-blocks is greater than the preset number.

First image sub-block inner product module is configured to calculate all the inner products of every two first image sub-blocks.

Blood vascular dictionary constructing sub-module is configured to select the preset number of first image sub-blocks with minimum inner product, and construct the blood vascular dictionary.

Image filtering and dividing module 2 is configured to apply Frangi-based filtering to retinal vessel images to be enhanced, and divides the obtained images having undergone Frangi-based filtering into a plurality of second image sub-blocks overlapped each other. Image filtering and dividing module 2 comprises smooth filtering module, Hessian matrix calculating module, eigenvalue analyzing module, Frangi-based filtering result generating module, and second image sub-block dividing module.

Smooth filtering module is configured to define the retinal vessel image to be enhanced as $I(x, y)$, and let $G(x, y; \sigma)$ be a two-dimensional Gaussian function at scale $\sigma$, smooth the retinal vessel image $I(x, y)$ to be enhanced using the two-dimensional Gaussian function, thereby obtaining a smoothed image $I_\sigma(x, y)$:

$I_\sigma(x, y) = I(x, y) \otimes G(x, y; \sigma)$, where $$G(x, y; \sigma) = \frac{1}{\left(\sqrt{2\pi}\,\sigma\right)^2} e^{-\frac{x^2+y^2}{2\sigma^2}},$$

and $\otimes$ denotes a convolutional operation;

Hessian matrix calculating module is configured to calculate a Hessian matrix $H_\sigma(x, y)$ at point $(x, y)$ and scale $\sigma$ in the smoothed image $I_\sigma(x, y)$:

$$H_\sigma(x, y) = \begin{bmatrix} \frac{\partial I_\sigma^2(x, y)}{\partial x^2} & \frac{\partial I_\sigma^2(x, y)}{\partial x \partial y} \\ \frac{\partial I_\sigma^2(x, y)}{\partial x \partial y} & \frac{\partial I_\sigma^2(x, y)}{\partial y^2} \end{bmatrix}.$$

Eigenvalue analyzing module is configured to performs an eigenvalue analysis of the Hessian matrix $H_\sigma(x, y)$, then obtain the eigenvalues $\lambda_1$ and $\lambda_2$, ordered as $|\lambda_1| < |\lambda_2|$; accordingly, the vascular feature at scale $s$ can be expressed by:

$$v_0(s) = \begin{cases} e^{-\frac{R_\beta^2}{2\beta}} \cdot \left(1 - e^{-\frac{S^2}{2c^2}}\right) & \lambda_2 \leq 0; \\ 0 & \lambda_2 > 0 \end{cases}$$

Where $$R_\beta = \frac{|\lambda_1|}{|\lambda_2|},$$

$S = \sqrt{\lambda_1^2 + \lambda_2^2}$; $\beta$ and $C$ are the preset constants;

Frangi-based filtering result generating module is configured to, in a multiscale framework, select the maximum value of $v_0(s)$ at each scale as a Frangi-based filtering result $v$ of the retinal vessel image $I(x, y)$ to be enhanced:

$$v = \max_{s_{min} \leq s \leq s_{max}} v_0(s)$$

Where $s_{min}$ and $s_{max}$ denote the minimum and maximum scales, respectively;

Second image sub-block dividing module is configured to divide the Frangi-based filtering result $v$ into a plurality of second image sub-blocks overlapped each other.

Blood vessel type determining module 5 is configured to apply directional filtering to the second image sub-block by means of a directional filter, and decide that the blood vessels contained in the second image sub-block belong to wide vessels or thin vessels based on directional filtering results. Blood vessel type determining module 5 comprises directional filter setting module, energy calculating module, energy difference calculating module, maximum energy difference determining module, and blood vessel type determining sub-module.

Directional filter setting module is configured to set up 8 directional filters in the directions $\theta_1 = 0$, $$\theta_2 = \frac{\pi}{8}, \theta_3 = \frac{\pi}{4}, \theta_4 = \frac{3\pi}{8}, \theta_5 = \frac{\pi}{2}, \theta_6 = \frac{5\pi}{8}, \theta_7 = \frac{3\pi}{4} \text{ and } \theta_8 = \frac{7\pi}{8},$$

respectively.

Energy calculating module is configured to, assuming that $\Omega_1$ is a vascular region by the directional filter in the direction $\theta_i$, $\Omega_2$ is a non-vascular region, thus calculate the respective energy $posE_{\theta_i}$ and $negE_{\theta_i}$ of the two region as follows:

$posE_{\theta_i} = \sum_{x=1}^{N_1} \sum_{y=1}^{N_1} |v(x,y)|^2, (x,y) \in \Omega_1;$ $negE_{\theta_i} = \sum_{x'=1}^{N_2} \sum_{y'=1}^{N_2} |v(x',y')|^2, (x',y') \in \Omega_2;$ where $v(x, y)$ is the value of the Frangi-based filtering result $v$ at point $(x, y)$, $N_1$ is the number of pixels in $\Omega_1$, and $N_2$ is the number of pixels in $\Omega_2$.

Energy difference calculating module is configured to calculate the energy difference between $posE_{\theta_i}$ and $negE_{\theta_i}$:

$E\theta_i = posE_{\theta_i} - negE_{\theta_i}.$

Maximum energy difference determining module determines the maximum energy difference among the above 8 directions:

$$E_{max} = \max_{i=1,2,\ldots,8} E\theta_i$$

Blood vessel type determining sub-module is configured to decide blood vessel types based on the $E_{max}$, if $E_{max} \geq T$, the retinal vessel image contained in the second image sub-block belongs to wide vessels, otherwise it belongs to thin vessels.

Vascular region and its residual error weight and residual error threshold determining module 4 is configured to determine a vascular region in the second image sub-block, and set residual error weight and residual error threshold of a vascular region in the second image sub-block according to blood vessel types contained in the second image sub-block. Vascular region and its residual error weight and residual error threshold determining module 4 comprises vascular region determining module and residual error weight and residual error threshold determining module.

Vascular region determining module is configured to take the vascular region by the directional filter corresponding to the maximum energy difference among the 8 directions as a vascular region $\Omega_1$, and take the non-vascular region by the directional filter corresponding to the maximum energy difference among the 8 directions as a non-vascular region $\Omega_2$;

Residual error weight and residual error threshold determining module is configured to, for the second image sub-block containing an retinal vessel image that belongs to wide vessels, set the residual error weight of the vascular region $\Omega_1$ to 1, such that the residual error threshold $T_R=T_1$; for the second image sub-block containing an retinal vessel image that belongs to thin vessels, set its residual error weight of the vascular region $\Omega_1$ to $1/v_{max}$, such that the residual error threshold $T_R=T_2$, where $v_{max}$ denotes the maximum value among Frangi-based filtering results of the second image sub-block.

Sparse coefficient calculating module 3 is configured to calculate the inner products between the second image sub-block and each first image sub-block in the blood vascular dictionary, determine a first image sub-block with maximum inner product among them, and calculate the sparse coefficient corresponding to the first image sub-block with maximum inner product. Sparse coefficient calculating module 3 comprises image vectorizing module, first image sub-block selecting module and sparse coefficient calculating sub-module.

Image vectorizing module is configured to vectorize the second image sub-block as x, and take $d_i$ as first No. i image sub-block in the blood vascular dictionary.

First image sub-block selecting module is configured to take a first image sub-block corresponding to the largest one of inner products between each first image sub-block in the blood vascular dictionary and the second image sub-block x as the selected No. 1 first image sub-block $d_{r0}$:

$$d_{r0} = \arg\max_{i \in (1,2,\ldots,k)} |<x, d_i>|;$$

Where k denotes the number of first image sub-blocks in the blood vascular dictionary, $r_0$ denotes an index number of the dictionary, and $<x, d_i>$ denotes the computation of inner product between x and $d_i$.

Sparse coefficient calculating submodule is configured to calculate the sparse coefficient $\alpha_{r0}$ corresponding to the first image sub-block $d_{r0}$:

$$\alpha_{r0} = <x, d_{r0}>,$$

it adds the index number $r_0$ of the selected first image sub-block $d_{r0}$ into the set S, such that $S = S \cup r0$.

Vascular region residual error calculating module 6 is configured to calculate a residual error image according to the first image sub-block with maximum inner product and the second image sub-block, and calculate the residual error of the vascular region in the second image sub-block according to the residual error weight of the vascular region. Vascular region residual error calculating module 6 comprises residual error preliminarily calculating module and residual error weighting module.

Residual error preliminarily calculating module is configured to calculate the residual error image R of the vascular region in the second image sub-block:

$$R = x - <x, d_{r0}> d_{r0};$$

Residual error weighting module is configured to multiply the residual error R by the residual error weight of the vascular region in the second image sub-block, and obtain the weighted sum as the final residual error of vascular region in the second image sub-block.

Jumping module 7 is configured to, when the norm of the residual error is greater than the residual error threshold, set the residual error image to a second image sub-block, and jump to the sparse coefficient calculating module 3, otherwise, jump to second image sub-block reconstructing module 8.

Second image sub-block reconstructing module 8 is configured to reconstruct the second image sub-block according to the sparse coefficient. The reconstructed second image sub-block is defined as:

$$\hat{x} = \sum_{r0 \in S} d_{r0} a_{r0}$$

Where S denotes a set of multiple sparse coefficients determined by the sparse coefficient calculating module multiple times, $d_{r0}$ denotes a first image sub-block with maximum inner product determined by the sparse coefficient calculating module each time and $\alpha_{r0}$ denotes a sparse coefficient corresponding to $d_{r0}$.

Retinal vessel image reconstructing module 9 is configured to reconstruct the retinal vessel image according to each reconstructed second image sub-block, and thereby obtaining an enhanced retinal vessel image. Retinal vessel image reconstructing module 9 is specifically used to:

merge non-overlapping parts of all the reconstructed second image sub-blocks, thereby obtaining a complete enhanced retinal vessel image. Specific operating principles of each module in the present system can be understood by reference to the corresponding steps in the aforementioned method for retinal vessel image enhancement.

The above descriptions are just preferred embodiments of the present invention, not for the purpose of limiting the invention, and any modification, equivalent substitution or improvement within the spirit and principles of the invention, should be included in the protection scope of the present invention.

What is claimed is:

1. A retinal vessel image enhancement method, comprising the following steps:
step A: constructing a blood vascular dictionary using retinal vessel learning images, wherein the blood vascular dictionary comprises a preset number of first image sub-blocks;
step B: applying Frangi-based filtering to a retinal vessel image to be enhanced, and dividing the obtained retinal vessel image into a plurality of second image sub-blocks overlapped each other;
step C: applying directional filtering to the second image sub-blocks by means of a directional filter, and deciding that the retinal vessels contained in the second image sub-blocks belong to wide vessels or thin vessels based on directional filtering results;

step D: determining a vascular region in each of the second image sub-blocks, and setting residual error weight and residual error threshold of a vascular region in each second image sub-block according to retinal vessel types contained in the second image sub-block;

step E: calculating inner products between each second image sub-block and each first image sub-block in the blood vascular dictionary, determining a first image sub-block with maximum inner product for each second image sub-block, and calculating a sparse coefficient corresponding to the first image sub-block with maximum inner product;

step F: for each second image sub-block, calculating a residual error image according to the first image sub-block with maximum inner product and the second image sub-block, and calculating the residual error of the vascular region in the second image sub-block according to the residual error weight of the vascular region;

step G: when a norm of the residual error is greater than a residual error threshold, setting the residual error image as a second image sub-block, and jumping to step E, otherwise, jumping to step H;

step H: reconstructing the second image sub-block according to the sparse coefficient;

step I: reconstructing the retinal vessel image according to each reconstructed second image sub-block, and thereby obtaining an enhanced retinal vessel image.

2. The retinal vessel image enhancement method according to claim 1, wherein the step A comprises the sub-steps of:

sub-step A1: partitioning the retinal vessel learning image into a plurality of first image sub-blocks with the same size; wherein the number of first image sub-blocks is greater than the preset number;

sub-step A2: calculating all the inner products of every two first image sub-blocks;

sub-step A3: selecting the preset number of first image sub-blocks with minimum inner product, and constructing the blood vascular dictionary.

3. The retinal vessel image enhancement method according to claim 1, wherein the step B comprises the sub-steps of:

sub-step B1: supposing the retinal vessel image to be enhanced as $I(x, y)$, and letting $G(x, y; \sigma)$ be a two-dimensional Gaussian function at scale $\sigma$, smoothing the retinal vessel image $I(x, y)$ to be enhanced using the two-dimensional Gaussian function, thereby obtaining a smoothed image $I_\sigma(x, y)$:

$I_\sigma(x, y) = I(x, y) \otimes G(x, y; \sigma)$, where $$G(x, y; \sigma) = \frac{1}{(\sqrt{2\pi}\sigma)^2} e^{-\frac{x^2+y^2}{2\sigma^2}},$$

and $\otimes$ denotes a convolutional operation;

sub-step B2: calculating a Hessian matrix $H_\sigma(x, y)$ at point $(x, y)$ and scale $\sigma$ in the smoothed image $I_\sigma(x, y)$:

$$H_\sigma(x, y) = \begin{bmatrix} \frac{\partial I_\sigma^2(x, y)}{\partial x^2} & \frac{\partial I_\sigma^2(x, y)}{\partial x \partial y} \\ \frac{\partial I_\sigma^2(x, y)}{\partial x \partial y} & \frac{\partial I_\sigma^2(x, y)}{\partial y^2} \end{bmatrix};$$

sub-step B3: performing an eigenvalue analysis of the Hessian matrix $H_\sigma(x, y)$, then obtaining the eigenvalues $\lambda_1$ and $\lambda_2$, ordered as $|\lambda_1|<|\lambda_2|$; accordingly, the vascular feature at scale s can be expressed by:

$$v_0(s) = \begin{cases} e^{-\frac{R_\beta^2}{2\beta}} \cdot \left(1 - e^{-\frac{S^2}{2c^2}}\right) & \lambda_2 \leq 0 \\ 0 & \lambda_2 > 0 \end{cases};$$

where $$R_\beta = \frac{|\lambda_1|}{|\lambda_2|},$$

$S=\sqrt{\lambda_1^2+\lambda_2^2}$, and $\beta$ and C are the preset constants;

sub-step B4: In a multiscale framework, selecting the maximum value of $v_0(s)$ at each scale as a Frangi-based filtering result v of the retinal vessel image $I(x, y)$ to be enhanced:

$$v = \max_{s_{min} \leq s \leq s_{max}} v_0(s)$$

where $s_{min}$ and $s_{max}$ denote the minimum and maximum scales, respectively;

sub-step B5: dividing the Frangi-based filtering result v into a plurality of second image sub-blocks overlapped each other.

4. The retinal vessel image enhancement method according to claim 1, wherein the step C comprises the sub-steps of:

sub-step C1: setting up 8 directional filters in the directions $\theta_1=0$, $$\theta_2 = \frac{\pi}{8}, \theta_3 = \frac{\pi}{4}, \theta_4 = \frac{3\pi}{8}, \theta_5 = \frac{\pi}{2}, \theta_6 = \frac{5\pi}{8}, \theta_7 = \frac{3\pi}{4} \text{ and } \theta_8 = \frac{7\pi}{8},$$

respectively;

sub-step C2: assuming that $\Omega_1$ is a vascular region by the directional filter in the direction $\theta_i$, $\Omega_2$ is a non-vascular region, the respective energy $posE_{\theta_i}$ and $negE_{\theta_i}$ of the two region is calculated as follows:

$posE_{\theta_i} = \Sigma_{x=1}^{N_2} \Sigma_{y=1}^{N_2} |v(x,y)|^2, (x,y) \in \Omega_1;$ $negE_{\theta_i} = \Sigma_{x'=1}^{N_2} \Sigma_{y'=1}^{N_2} |v(x',y')|^2, (x',y') \in \Omega_2;$ where $v(x, y)$ is the value of the Frangi-based filtering result v at point $(x, y)$, $N_1$ is the number of pixels in $\Omega_1$, and $N_2$ is the number of pixels in $\Omega_2$;

sub-step C3: calculating an energy difference between $posE_{\theta_i}$ and $negE_{\theta_i}$:

$E\theta_i = posE_{\theta_i} - negE_{\theta_i};$ sub-step C4: determining a maximum energy difference among the above 8 directions:

$$E_{max} = \max_{i=1,2,\ldots,8} E\theta_i;$$

sub-step C5: deciding retinal vessel types based on the $E_{max}$, when $E_{max} \geq T$, the retinal vessel image contained in the second image sub-block belongs to wide vessels, otherwise it belongs to thin vessels.

5. The retinal vessel image enhancement method according to claim 3, wherein the step D comprises the sub-steps of:

sub-step D1: taking the vascular region by the directional filter corresponding to the maximum energy difference among the 8 directions as a vascular region $\Omega_1$, and taking the non-vascular region by the directional filter corresponding to the maximum energy difference among the 8 directions as a non-vascular region $\Omega_2$;

sub-step D2: for the second image sub-block containing an retinal vessel image that belongs to wide vessels, setting the residual error weight of the vascular region $\Omega_1$ in the second image sub-block to 1, such that the residual error threshold $T_R=T_1$; for the second image sub-block containing an retinal vessel image that belongs to thin vessels, setting its residual error weight of the vascular region $\Omega_1$ to $1/v_{max}$, such that the residual error threshold $T_R=T_2$, where $v_{max}$ denotes the maximum value among Frangi-based filtering results of the second image sub-block.

6. The retinal vessel image enhancement method according to claim 1, wherein the step E comprises the sub-steps of:

sub-step E1: Vectorizing the second image sub-block as x, and let $d_i$ be first No. i image sub-block in the blood vascular dictionary;

sub-step E2: taking a first image sub-block corresponding to the largest one of inner products between each first image sub-block in the blood vascular dictionary and the second image sub-block x as the selected No. 1 first image sub-block $d_{r0}$:

$$d_{r0} = \arg \max_{i \in (1,2,\ldots,k)} | <x, d_i> |;$$

Where k denotes the number of first image sub-blocks in the blood vascular dictionary, $r_0$ denotes an index number of the dictionary, and $<x, d_i>$ denotes the computation of inner product between x and $d_i$;

sub-step E3: calculating the sparse coefficient $\alpha_{r0}$ corresponding to the first image sub-block $d_{r0}$:

$$\alpha_{r0} = <x, d_{r0}>.$$

7. The retinal vessel image enhancement method according to claim 1, wherein the step F comprises the sub-steps of:
sub-step F1: calculating calculating a residual error image R of the vascular region in the second image sub-block;
sub-step F2; multiplying the residual error image R by the residual error weight of the vascular region in the second image sub-block, and obtaining the weighted sum as calculating an final residual error of vascular region in the second image sub-block.

8. The retinal vessel image enhancement method according to claim 1, wherein the reconstructed second image sub-block is defined as:

$$\hat{x} = \sum_{r0 \in S} d_{r0} \alpha_{r0}$$

where S denotes a set of multiple sparse coefficients determined by multiple execution of step E, $d_{r0}$ denotes a first image sub-block with maximum inner product determined by execution of step E each time and $\alpha_{r0}$ denotes a sparse coefficient corresponding to $d_{r0}$.

9. The retinal vessel image enhancement method according to claim 1, wherein the Step I comprises the following:
merging non-overlapping parts of all the reconstructed second image sub-blocks, thereby obtaining a complete enhanced retinal vessel image.

10. A retinal vessel image enhancement system, comprising:

blood vascular dictionary constructing module, which is configured to construct a blood vascular dictionary using retinal vessel learning images, wherein the blood vascular dictionary comprises a preset number of first image sub-blocks;

image filtering and dividing module, which is configured to apply Frangi-based filtering to a retinal vessel image to be enhanced, and divide the obtained retinal vessel images having undergone Frangi-based filtering into a plurality of second image sub-blocks overlapped each other;

blood vessel type determining module, which is configured to apply directional filtering to the second image sub-blocks by means of a directional filter, and decide that the blood vessels contained in the second image sub-blocks belong to wide vessels or thin vessels based on directional filtering results; vascular region and its residual error weight and residual error threshold determining module, which is configured to determine a vascular region in each second image sub-block, and set residual error weight and residual error threshold of a vascular region in the second image sub-block according to blood vessel types contained in each second image sub-block;

sparse coefficient calculating module, which is configured to calculate, for each second image sub-block, the inner products between the second image sub-block and each first image sub-block in the blood vascular dictionary, determine a first image sub-block with maximum inner product among them, and calculate a sparse coefficient corresponding to the first image sub-block with maximum inner product; vascular region residual error calculating module, which is configured to calculate, for each second image sub-block, a residual error image according to the first image sub-block with maximum inner product and the second image sub-block, and calculate the residual error of the vascular region in the second image sub-block according to the residual error weight of the vascular region; jumping module, which is configured to, when a norm of the residual error is greater than a residual error threshold, set the residual error image as a second image sub-block, and jump to the sparse coefficient calculating module, otherwise, jump to second image sub-block reconstructing module; second image sub-block reconstructing module, which is configured to reconstruct the second image sub-block according to the sparse coefficient; retinal vessel image reconstructing module, which is configured to reconstruct the retinal vessel image according to each reconstructed second image sub-block, and thereby obtaining an enhanced retinal vessel image.

11. The retinal vessel image enhancement system according to claim 10, wherein the blood vascular dictionary constructing module comprises:

retinal vessel learning image dividing module, which is configured to partition the retinal vessel learning image into several first image sub-blocks with the same size; and the number of first image sub-blocks is greater than the set number;

first image sub-block inner product module, which is configured to calculate all the inner products of every two first image sub-blocks;

blood vascular dictionary constructing submodule, which is configured to select the preset number of first image sub-blocks with minimum inner product, and construct the blood vascular dictionary.

12. The retinal vessel image enhancement system according to claim 10, wherein the image filtering and dividing module comprises:

smooth filtering module, which is configured to define the retinal vessel image to be enhanced as I(x, y), and let G(x, y; σ) be a two-dimensional Gaussian function at scale σ, smooth the retinal vessel image I(x, y) to be enhanced using the two-dimensional Gaussian function, thereby obtaining a smoothed image $I_\sigma(x, y)$:

$I_\sigma(x, y) = I(x, y) \otimes G(x, y; \sigma)$, where $$G(x, y; \sigma) = \frac{1}{(\sqrt{2\pi}\,\sigma)^2} e^{-\frac{x^2+y^2}{2\sigma^2}},$$

and $\otimes$ denotes convolutional operation;

Hessian matrix calculating module, which is configured to calculate a Hessian matrix $H_\sigma(x, y)$ at point (x, y) and scale σ in the smoothed image $I_\sigma(x, y)$:

$$H_\sigma(x, y) = \begin{bmatrix} \frac{\partial I_\sigma^2(x, y)}{\partial x^2} & \frac{\partial I_\sigma^2(x, y)}{\partial x \partial y} \\ \frac{\partial I_\sigma^2(x, y)}{\partial x \partial y} & \frac{\partial I_\sigma^2(x, y)}{\partial y^2} \end{bmatrix};$$

eigenvalue analyzing module, which is configured to perform an eigenvalue analysis of the Hessian matrix $H_\sigma(x, y)$, then obtain the eigenvalues $\lambda_1$ and $\lambda_2$, ordered as $|\lambda_1| < |\lambda_2|$; accordingly, the vascular feature at scale s can be expressed by:

$$v_0(s) = \begin{cases} e^{-\frac{R_\beta^2}{2\beta}} \cdot \left(1 - e^{-\frac{S^2}{2C^2}}\right) & \lambda_2 \leq 0 \\ 0 & \lambda_2 > 0 \end{cases};$$

where $$R_\beta = \frac{|\lambda_1|}{|\lambda_2|},$$

$S = \sqrt{\lambda_1^2 + \lambda_2^2}$, and β and C are the preset constants;

Frangi-based filtering result generating module, which is configured to, in a multiscale framework, select the maximum value of $v_0(s)$ at each scale as a Frangi-based filtering result v of the retinal vessel image I(x, y) to be enhanced:

$$v = \max_{s_{min} \leq s \leq s_{max}} v_0(s)$$

where $s_{min}$ and $s_{max}$ denote the minimum and maximum scales, respectively;

second image sub-block dividing module, which is configured to divide the Frangi-based filtering result v into a plurality of second image sub-blocks overlapped each other.

13. The retinal vessel image enhancement system according to claim 10, wherein the blood vessel type determining module comprises:

directional filter setting module, which is configured to set up 8 directional filters in the directions $\theta_1 = 0$, $$\theta_2 = \frac{\pi}{8}, \theta_3 = \frac{\pi}{4}, \theta_4 = \frac{3\pi}{8}, \theta_5 = \frac{\pi}{2}, \theta_6 = \frac{5\pi}{8}, \theta_7 = \frac{3\pi}{4} \text{ and } \theta_8 = \frac{7\pi}{8},$$

respectively;

energy calculating module, which is configured to, assuming that $\Omega_1$ is a vascular region by the directional filter in the direction $\theta_i$, $\Omega_2$ is a non-vascular region, thus calculate the respective energy $posE_{\theta_i}$ and $negE_{\theta_i}$ of the two region as follows:

$posE_{\theta_i} = \sum_{x=1}^{N_1} \sum_{y=1}^{N_1} |v(x,y)|^2, (x,y) \in \Omega_1$;

$negE_{\theta_i} = \sum_{x'=1}^{N_2} \sum_{y'=1}^{N_2} |v(x',y')|^2, (x',y') \in \Omega_2$;

where v(x, y) is the value of the Frangi-based filtering result v at point (x, y), $N_1$ is the number of pixels in $\Omega_1$, and $N_2$ is the number of pixels in $\Omega_2$;

energy difference calculating module, which is configured to calculate the energy difference between $posE_{\theta_i}$ and $negE_{\theta_i}$:

$E\theta_i = posE_{\theta_i} - negE_{\theta_i}$;

maximum energy difference determining module, which is configured to determine the maximum energy difference among the above 8 directions:

$$E_{max} = \max_{i=1,2,\ldots,8} E\theta_i;$$

blood vessel type determining submodule, which is configured to decide blood vessel types based on the $E_{max}$, when $E_{max} \geq T$, the retinal vessel image contained in the second image sub-block belongs to wide vessels, otherwise it belongs to thin vessels.

14. The retinal vessel image enhancement system according to claim 13, wherein the vascular region and its residual error weight and residual error threshold determining module comprises:

vascular region determining module, which is configured to take the vascular region by the directional filter corresponding to the maximum energy difference among the 8 directions as a vascular region $\Omega_1$, and take the non-vascular region by the directional filter corresponding to the maximum energy difference among the 8 directions as a non-vascular region $\Omega_2$;

residual error weight and residual error threshold determining module which is configured to, for the second image sub-block containing an retinal vessel image that belongs to wide vessels, set the residual error weight of the vascular region $\Omega_1$ to 1, such that the residual error threshold $T_R=T_1$; for the second image sub-block containing an retinal vessel image that belongs to thin vessels, set its residual error weight of the vascular region $\Omega_1$ to $1/v_{max}$, such that the residual error threshold $T_R=T_2$, where $v_{max}$ denotes the maximum value among Frangi-based filtering results of the second image sub-block.

15. The retinal vessel image enhancement system according to claim 10, wherein the sparse coefficient calculating module comprises:
   image vectorizing module, which is configured to vectorize the second image sub-block as x, and take $d_i$ as first No. i image sub-block in the blood vascular dictionary;
   first image sub-block selecting module, which is configured to take a first image sub-block corresponding to the largest one of inner products between each first image sub-block in the blood vascular dictionary and the second image sub-block x as the selected No. 1 first image sub-block $d_{r0}$:

$$d_{r0} = \arg\max_{i\in(1,2,\ldots,k)} |<x, d_i>|;$$

where k denotes the number of first image sub-blocks in the blood vascular dictionary, $r_0$ denotes an index number of the dictionary, and $<x, d_i>$ denotes the computation of inner product between x and $d_i$;
   sparse coefficient calculating submodule, which is configured to calculate the sparse coefficient $\alpha_{r0}$ corresponding to the first image sub-block $d_{r0}$:

$$\alpha_{r0}=<x,d_{r0}>.$$

16. The retinal vessel image enhancement system according to claim 10, wherein the vascular region residual error calculating module comprises:
   residual error preliminarily calculating module, which is configured to calculate the residual error image R of the vascular region in the second image sub-block:

$$R=x-<x,d_{r0}>d_{r0};$$

residual error weighting module, which is configured to multiply the residual error R by the residual error weight of the vascular region in the second image sub-block, and obtain the weighted sum as the final residual error of vascular region in the second image sub-block.

17. The retinal vessel image enhancement system according to claim 10, wherein the reconstructed second image sub-block is defined as:

$$\hat{x} = \sum_{r0\in S} d_{r0}\alpha_{r0}$$

where S denotes a set of multiple sparse coefficients determined by the sparse coefficient calculating module multiple times, $d_{r0}$ denotes a first image sub-block with maximum inner product determined by the sparse coefficient calculating module each time and $\alpha_{r0}$ denotes a sparse coefficient corresponding to $d_{r0}$.

18. The retinal vessel image enhancement system according to claim 10, wherein the retinal vessel image reconstructing module is specifically used to:
   merge non-overlapping parts of all the reconstructed second image sub-blocks, thereby obtaining a complete enhanced retinal vessel image.

* * * * *